United States Patent [19]
Anderson

[11] Patent Number: 5,989,267
[45] Date of Patent: *Nov. 23, 1999

[54] METHOD OF HAIR REMOVAL

[75] Inventor: Richard Rox Anderson, Lexington, Mass.

[73] Assignee: The General Hospital Corporation, Boston, Mass.

[ * ] Notice: This patent is subject to a terminal disclaimer.

[21] Appl. No.: 08/893,856

[22] Filed: Jul. 11, 1997

Related U.S. Application Data

[63] Continuation of application No. 08/314,082, Sep. 28, 1994, Pat. No. 5,669,916.

[51] Int. Cl.⁶ .................................................. A61B 17/50
[52] U.S. Cl. ........................... 606/133; 606/134; 606/43
[58] Field of Search ............................. 606/133, 43, 134, 606/36

[56] References Cited

U.S. PATENT DOCUMENTS

| | | |
|---|---|---|
| 3,538,919 | 11/1970 | Meyer . |
| 3,794,028 | 2/1974 | Mueller et al. . |
| 4,317,450 | 3/1982 | Chalmers et al. . |
| 4,388,926 | 6/1983 | Weissman et al. . |
| 4,617,926 | 10/1986 | Sutton . |
| 4,693,885 | 9/1987 | Bommer et al. . |
| 4,977,177 | 12/1990 | Bommer et al. . |
| 5,026,369 | 6/1991 | Cole .......................................... 606/43 |
| 5,059,192 | 10/1991 | Zaias . |
| 5,079,262 | 1/1992 | Kennedy et al. . |
| 5,211,938 | 5/1993 | Kennedy et al. . |
| 5,219,878 | 6/1993 | Ringuet et al. . |
| 5,226,907 | 7/1993 | Tankovich . |
| 5,234,940 | 8/1993 | Kennedy et al. . |
| 5,376,088 | 12/1994 | Glaros ........................................ 606/36 |
| 5,669,916 | 9/1997 | Anderson ................................ 606/133 |

OTHER PUBLICATIONS

Kennedy J.C. et al., "Photodynamic Therapy with Endogenous Procoparphyrin IX: Basic Principles and Present Clinical Experience"; *Elsevier Sequoia* 6:143–148 (1990.

*Primary Examiner*—Michael Buiz
*Assistant Examiner*—Kevin Truong
*Attorney, Agent, or Firm*—Fish & Richardson P.C.

[57] ABSTRACT

The invention features a method of removing a hair, involving mechanically or chemically removing the hair to expose the follicle of the hair, and then treating the follicle to inhibit its ability to regenerate a hair. Removing the hair facilitates the uptake of a follicle-inactivating compound and thus allows for long-term inhibition of hair growth.

15 Claims, 1 Drawing Sheet

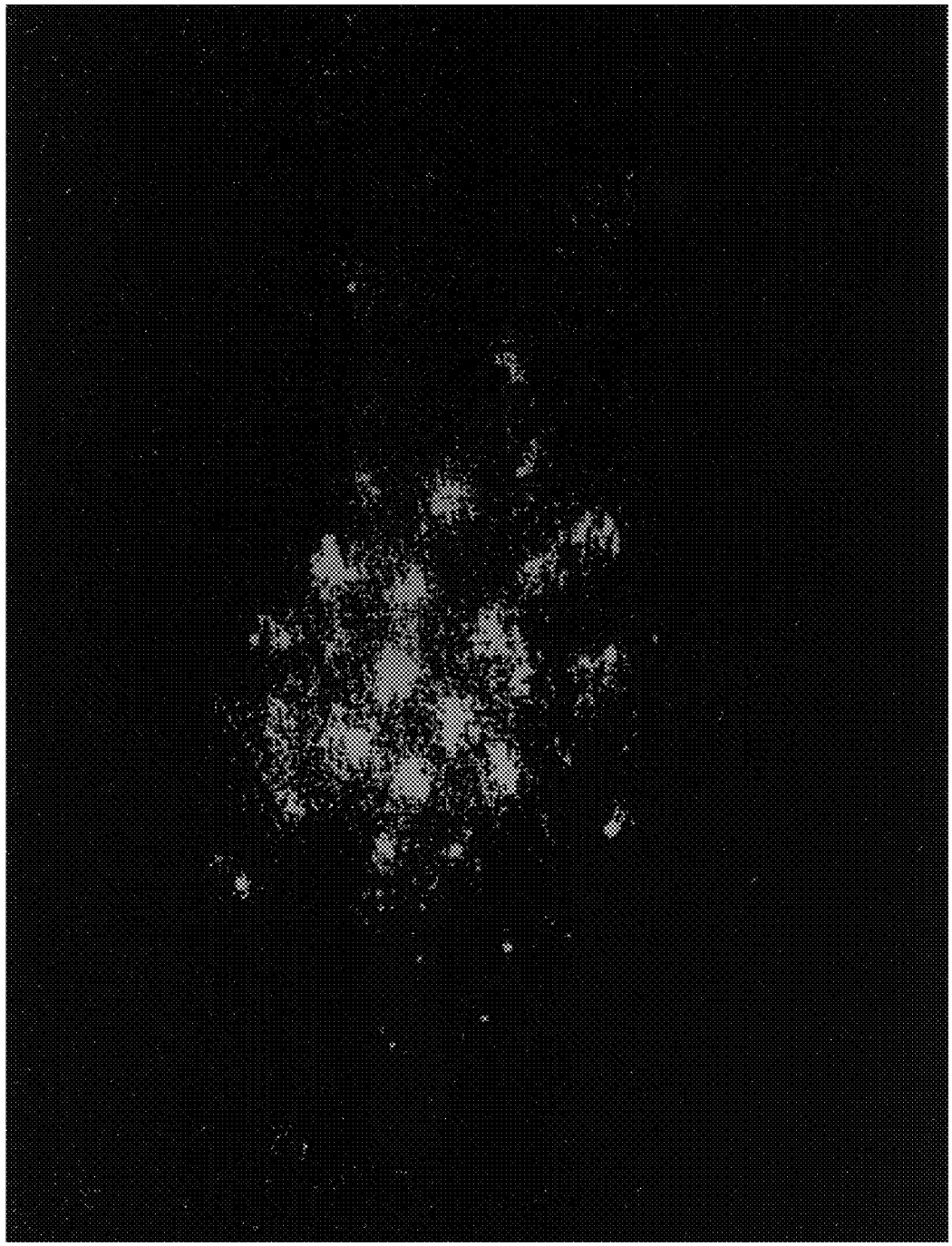
FIGURE

METHOD OF HAIR REMOVAL

This is a continuation of application Ser. No. 08/314,082, filed Sep. 28, 1994, now U.S. Pat. No. 5,669,916.

This invention was made at least in part with funds from the Federal government under contract N00014-91-C-0084 awarded by the Department of the Navy. The Government therefore has certain rights in the invention.

BACKGROUND OF THE INVENTION

This invention relates to removing hair from skin.

Currently used methods for hair removal include shaving, waxing, electrolysis, mechanical epilation, chemical depilation, the use of laser beams (see, e.g., U.S. Pat. Nos. 3,538,919 and 4,388,924), and the use of light-absorbing substances (see, e.g., U.S. Pat. No. 5,226,907). Some of these methods are painful, inefficient, or time consuming, and others do have not long-lasting effects.

SUMMARY OF THE INVENTION

I have discovered that mechanical epilation followed by topical applications causing inactivation of the hair follicle results in long-term inhibition of hair growth.

Accordingly, the invention features a method of removing a hair from the skin of a mammal, involving mechanically or chemically epilating to expose the hair follicle, then treating the follicle to inhibit its ability to regenerate a hair.

Epilation creates a channel which leads directly and deeply into the follicle and greatly increases the ability of the follicle to take up agents which can inactivate the hair growth-promoting properties of the follicle. Thus, the invention provides an efficient method for the removal of hair and for long-term inhibition of hair growth.

In preferred embodiments, epilation is performed using any method which removes the hair from its follicle, including cold waxing, warm waxing, and the use of mechanical devices to avulse the hair from its follicle.

Following epilation, the hair growth-promoting properties of the follicle are inactivated by any of a plurality of methods, including the use of photosensitizers followed by exposure to light, the use of mild toxins, and application of electric current. Generally, photoinactivation involves (1) application of a photosensitizer to the skin, (2) uptake of the photosensitizer by the follicle, and (3) activation of the photosensitizer so that it inactivates the hair growth-promoting properties of the follicle, resulting in inhibition of hair growth. Preferably, the photosensitizer is of low toxicity until it is activated by exposure to light of a specific wavelength. Preferably, the light is at a wavelength which is capable of reaching deep into the hair follicle; generally, a wavelength of 550–800 nm is suitable. Preferred photosensitizers include, but are not limited to, porphyrins, phthalocyanines, chlorins, and purpurins. Examples of suitable photosensitizers are aminolevulinic acid (ALA; activated at 630 nm), methlyene blue (activated at 660 nm), derivatives of nile blue-A, porphyrin derivatives such as benzoporphyrin derivative (BPD; activated at 690 nm), porfimer sodium (e.g., PHOTOFRIN™ porfimer sodium; activated at 630 nm), purpurins, chlorins, and phthalocyanines. The photosensitizer can act by either photochemical or photothermal mechanisms. Photothermal sensitizers include indocyanine green (activated at 690–800 nm) and other dyes.

Mild toxins can also be used to inactivate the hair follicle. In this embodiment, epilation of the hair prior to application of the toxin results in the targeting of the toxin to the follicle. The toxin is allowed to interact with the hair follicle for a period of time sufficient to inactivate the follicle without causing substantial damage (e.g., ulceration or scarring) to the surrounding skin; generally, 0.1–5 minutes is a sufficient length of time. Appropriate toxins include, but are not limited to, bleaches (e.g., hypochlorites and peroxides), antimetabolic drugs (e.g., 5-fluorouracil), solvents (e.g., acetone, alcohols, phenol, and ethers), iodine-releasing agents, detergents and surfactants, and aldehydes and other protein-crosslinking fixatives (e.g., gluteraldehyde, formaldehyde, and acetaldehyde).

In addition, more than one toxin can be used in the invention, with application of the toxins occurring sequentially or simultaneously (e.g., a surfactant, a solvent, and an antimetabolic drug can be combined or used in sequence). One skilled in the art of dermatology will, with the guidance provided herein, be able to determine the appropriate conditions required for uptake of the toxin.

The method of the invention can also employ iontophoretic techniques to target the follicle-inactivating compound to the hair follicle. In this embodiment, a solution which includes an ionic follicle-inactivating compound is applied to the skin following epilation, and an electric current is then applied to the skin. The electric current enhances the ability of the follicle-inactivating compound to penetrate the skin. Useful solutions include, but are not limited to, hypochlorite bleach, chloride salt solutions, ionic detergents, and ionic photosensitizers or their precursors (e.g., ALA and methylene blue). Appropriate methods and devices for applying electric current are known in the art (see, e.g., Instructions for use by Iomed Inc., Salt Lake City, Utah). Anesthetics (e.g., lidocaine) can also be iontophoresed in order to alleviate pain in this embodiment of the invention. A variety of other methods, including ultrasound or pressure waves, heating, surfactants, and simple capillary action, can also be used to target the follicle-inactivating compound to the follicle.

By "epilation" is meant removal of the hair from its follicle. Epilation can be accomplished by chemical or mechanical means, such as cold waxing, warm waxing, or grasping the hair and detaching it to expose the follicle.

By "hair follicle" is meant the downgrowth of the epidermis and the bulb-like expansion of tissue which houses and creates a hair. Components of the hair follicle include the external root sheath, the internal root sheath, the connective tissue papilla, the matrix, the pluripotential cells which are located approximately 1 mm below the skin surface, and sebaceous glands.

By "inactivation" of the hair follicle is meant inhibition of the follicle's ability to regenerate a hair and/or the sebaceous glands which are part of the hair follicle on the face, uppertrunk, and other body sites prone to acne. Inhibition of hair growth can be accomplished by destruction of one or more components of the follicle. The exact target to be destroyed can vary depending on the composition used to inactivate the hair follicle. Candidate components to be destroyed include, but are not limited to, the external root sheath, the internal root sheath, the connective tissue papilla, the matrix, the sebaceous glands, and the pluripotential cells which are located approximately 1 mm below the skin surface.

By "photosensitizer" is meant a compound which, in response to exposure to a particular fluence, is capable of inactivating a hair follicle, or a precursor of such a compound which is converted into a photosensitizer in living cells (e.g., ALA).

By "activation" of a photosensitizer or photosensitizer precursor is meant exposure of the photosensitizer or precursor to light in either a pulse or continuous mode, enabling the photosensitizer to inactivate a hair follicle.

Abbreviations used herein are
ALA: aminolevulinic acid
BPD: benzoporphyrin derivative
PPIX: protoporphyrin IX Other features and advantages of the invention will be apparent from the following description of the preferred embodiments thereof, and from the claims.

DETAILED DESCRIPTION

The drawing will first be described.

Drawing

The Figure is a fluorescence image of PPIX in human skin following local epilation and application of 20% ALA.

SELECTIVE ABSORPTION BY EPILATED FOLLICLES

Epilation leads to selective uptake of follicle-inactivating compounds by the exposed follicles.

In the following procedure, epilation was accomplished by cold waxing a segment of skin of a human subject in order to remove the hair. Cold waxing is performed by application of a viscous, liquid wax or resin mixture (e.g., MYEPIL™ wax) which, when rapidly uplifted, avulses each hair from its follicle. As a control, other sites on the skin were shaved, but not epilated, and all sites on the skin were then treated as follows. A solution of 20% (wt./wt.) of the photosensitizer, ALA, was applied to the skin in an ethanol/water solution, and the treated skin was covered with plastic wrap for 2–4 hours. ALA is a precursor of protoporphyrin IX (PPIX), and it is converted into PPIX in living cells. Thus, the 2–4 hour time period is sufficient for uptake of ALA by the epilated follicle (which occurs within minutes) and conversion of ALA into PPIX. The absorption of ALA and its conversion to PPIX in the skin was followed by fluorescence imaging (420 nm excitation; 600+ nm emission). The intense fluorescence shown in the center of the Figure indicates that cells of the epilated follicles can convert ALA into PPIX. This image also indicates that epilation enables the photochemical to selectively penetrate the follicles of epilated follicles (located at the center of the Figure) as compared with non-epilated follicles. Thus, epilation facilitates targeting of the inactivating agent to the follicle.

Inhibition of Hair Growth

Following epilation or shaving (as a control), and application of ALA, the hair follicles were inactivated by exposing the skin to varying fluences from 0–300 J/cm$^2$ of 630 nm (argon-pumped dye laser) light. At 3 and 6 months after treatment, the number of regrowing hairs varied from 0% to about 50%. In contrast, 100% of the hairs on shaven, but not epilated, skin regrew. These data also indicate that the effectiveness of the method increased with increasing fluence.

OTHER EMBODIMENTS

Other embodiments are within the following claims. For example, a mechanical device, instead of waxing, can be used to remove the hair from the follicle. Chemical agents, e.g., chemical depilatory cremes which break disulfide bonds in the hair shaft, can be used as well.

Photosensitizers other than ALA can be used to inactivate the hair follicle; examples include porphyrins, phthalocyanines, chlorins, purpurins, and derivatives of rhodamine or nile blue. Indeed, I have found evidence of selective follicle destruction following topical application of methylene blue, enhancement of uptake by iontophoresis, and exposure to light at 660 nm. I also have detected follicle destruction following application of chloroaluminum sulforated phthalocyanine and exposure to light at 760 nm. Thus, the usefulness of this invention is not limited to ALA. Generally, a photosensitizer concentration of 0.1 to 20% is appropriate; more preferably, the concentration is about 0.5 to 5%; most preferably, the concentration is about 1%. Several examples of useful photosensitizers and the appropriate wavelength of light are provided herein; additional examples will be apparent to those of skill in the art of photochemistry.

Mild toxins such as bleaches, antimetabolic drugs, solvents, iodine-releasing agents, detergents, surfactants, and protein-crosslinking fixatives can be used at concentrations which inactivate the follicle without causing substantial damage (e.g., scarring and ulceration) to the surrounding skin. Generally, concentrations of 1 to 20% are suitable, with absorption by the follicle typically lasting 0.1 to 5 minutes.

A variety of dematologically acceptable excipients (e.g., alcoholic and aqueous solutions, oil-in-water or water-in-oil creams, emulsions, or ointments) can be used to carry the follicle-inactivating compound, and acceptable forms of the excipient include, without limitation, lotions, creams, and liquids. The vehicle used should carry the photosensitizer or toxin into the follicle, which is best achieved when a low surface tension exists between the vehicle and the skin to promote capillary action. The follicle-inactivating compositions can be delivered to the follicle by methods other than simple capillary action, such as those methods which employ ultrasound, heat, pressure waves, iontophoresis, or surfactants. The amount of time necessary for uptake of the follicle-inactivating composition will depend on factors such as the method of application, the properties of the follicle-inactivating compound, and the excipient which is used. Generally, the amount of time sufficient for uptake of the follicle-inactivating compound is 1 to 5 minutes.

Iontophoresis can also be used to facilitate uptake of the follicle-inactivating compound by the follicle. In skin, the stratum corneum acts as a barrier to electrical resistance. Following epilation, the empty follicles are the predominant pathway by which current flows from an external electrolyte solution into the skin. Therefore, iontophoresis can enhance the uptake of ionic follicle-inactivating compounds. In this embodiment, an electrode of the same polarity as the compound to be iontophoresed is applied to the skin following application of the follicle-inactivating compound. (see, instructions for use of iontophoresis by Iomed Inc., Salt Lake City, Utah). Examples of ionic follicle-inactivating compounds are ALA, methylene blue, hypochlorite bleach, chloride salt solutions, and ionic detergents.

Generally, photosensitizer precursors (e.g., ALA) are converted into the photosensitizer (e.g., PPIX) within 2–4 hours. The ability of the photosensitizer precursors to be absorbed by the follicle and converted into the photosensitizer by cells of the follicle can readily be assayed by fluorescence imaging as described above. For improved light coupling into the skin, a layer of mineral oil can be applied to the skin and covered by a lucite block or other transparent material which closely matches the skin's refractive index while activating the photosensitizer with light. The optimal conditions for hair removal and follicle inactivation can easily be determined by testing the method on a small segment of the skin and monitoring the skin for subsequent hair growth.

What is claimed is:

1. A method of removing a hair from the skin of a mammal, the method comprising
   (a) applying to the hair a chemical agent that removes the hair from its follicle, and then
   (b) treating the follicle to inhibit its ability to regenerate a hair.

2. The method of claim 1, wherein the chemical agent breaks disulfide bonds in the hair.

3. The method of claim 1, wherein step (b) comprises applying a toxin to the follicle.

4. The method of claim 3, wherein the toxin is an antimetabolic drug.

5. The method of claim 4, wherein the antimetabolic drug is 5-fluorouracil.

6. The method of claim 3, wherein the toxin is a bleach.

7. The method of claim 4, wherein the bleach comprises a hypochlorite.

8. The method of claim 4, wherein the bleach comprises a peroxide.

9. The method of claim 1, wherein step (b) comprises application of a follicle-inactivating compound and ultrasound waves to the skin, the ultrasound waves being sufficient to target the follicle-inactivating compound to the hair follicle.

10. The method of claim 1, wherein step (b) comprises application of a follicle-inactivating compound and pressure waves to the skin, the pressure waves being sufficient to target the follicle-inactivating compound to the hair follicle.

11. The method of claim 1, wherein step (b) comprises application of a follicle-inactivating compound and heat to the skin, the heat being sufficient to target the follicle-inactivating compound to the hair follicle.

12. A method of removing a hair from the skin of a mammal, the method comprising
    (a) mechanically or chemically removing the hair from its follicle, and then
    (b) treating the follicle with a follicle-inactivating compound.

13. The method of claim 12, wherein step (b) further comprises application of ultrasound waves to the skin, the ultrasound waves being sufficient to target the follicle-inactivating compound to the hair follicle.

14. The method of claim 12, wherein step (b) further comprises application of pressure waves to the skin, the pressure waves being sufficient to target the follicle-inactivating compound to the hair follicle.

15. The method of claim 12, wherein step (b) further comprises application of heat to the skin, the heat being sufficient to target the follicle-inactivating compound to the hair follicle.

* * * * *